(12) United States Patent
Bouchard

(10) Patent No.: US 10,548,833 B2
(45) Date of Patent: Feb. 4, 2020

(54) USE OF A COMBINATION OF AN ASSOCIATIVE NONIONIC POLYETHER POLYURETHANE AND A CYCLOHEXANOL DERIVATIVE AS A SKIN REFRESHING AGENT

(71) Applicant: L'OREAL, Paris (FR)

(72) Inventor: Fabienne Bouchard, Montrouge (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/535,594

(22) PCT Filed: Dec. 15, 2015

(86) PCT No.: PCT/EP2015/079901
§ 371 (c)(1),
(2) Date: Jun. 13, 2017

(87) PCT Pub. No.: WO2016/096928
PCT Pub. Date: Jun. 23, 2016

(65) Prior Publication Data
US 2017/0367965 A1    Dec. 28, 2017

(30) Foreign Application Priority Data

Dec. 15, 2014 (FR) ...................... 14 62421

(51) Int. Cl.
| | | |
|---|---|---|
| *A61K 8/00* | (2006.01) | |
| *A61K 8/87* | (2006.01) | |
| *A61Q 13/00* | (2006.01) | |
| *A61Q 15/00* | (2006.01) | |
| *A61K 8/34* | (2006.01) | |
| *A61K 8/81* | (2006.01) | |

(52) U.S. Cl.
CPC ............... *A61K 8/87* (2013.01); *A61K 8/34* (2013.01); *A61K 8/8111* (2013.01); *A61Q 13/00* (2013.01); *A61Q 15/00* (2013.01)

(58) Field of Classification Search
None
See application file for complete search history.

(56) References Cited

U.S. PATENT DOCUMENTS

| | | | | |
|---|---|---|---|---|
| 5,695,746 A | * | 12/1997 | Garlick, Jr. ............... | A61K 8/34 424/49 |
| 5,912,294 A | * | 6/1999 | Schade ....................... | C08J 3/03 523/340 |
| 2004/0082654 A1 | * | 4/2004 | Pesce ....................... | A61K 8/37 514/547 |
| 2005/0053632 A1 | * | 3/2005 | Schafer ................... | A61K 8/361 424/401 |
| 2012/0322876 A1 | * | 12/2012 | Kermorvan ............ | A61K 8/365 514/573 |
| 2014/0248227 A1 | | 9/2014 | Doering et al. | |
| 2016/0000681 A1 | | 1/2016 | Aubrun et al. | |

FOREIGN PATENT DOCUMENTS

| | | |
|---|---|---|
| DE | 10 2011 086923 A1 | 5/2013 |
| EP | 0 988 852 A2 | 3/2000 |
| EP | 1550435 A1 | 7/2005 |
| FR | 3 002 140 A1 | 8/2014 |
| WO | WO-2014/050487 A1 | 4/2014 |

* cited by examiner

Primary Examiner — Susan T Tran
(74) Attorney, Agent, or Firm — Polsinelli PC

(57) ABSTRACT

The present invention relates to the cosmetic use as a skin refreshing agent of the combination of at least one associative nonionic polyether polyurethane and at least one cyclohexanol derivative.
The present invention also relates to a cosmetic method for refreshing the skin, consisting in applying to the skin surface a composition comprising, in particular in a cosmetically acceptable medium:
a) an aqueous phase; and
b) at least one associative nonionic polyether polyurethane; and
c) at least one cyclohexanol derivative.
The present invention also relates to a composition comprising, particularly in a physiologically acceptable medium:
a) at least one aqueous phase; and
b) at least one associative nonionic polyether polyurethane; and
c) at least one cyclohexanol derivative; and
d) at least one antiperspirant active agent.
The present invention also relates to a method for the treatment of human perspiration, and optionally of body odors, which consists in applying to the surface of the skin a composition as described previously.

25 Claims, No Drawings

USE OF A COMBINATION OF AN ASSOCIATIVE NONIONIC POLYETHER POLYURETHANE AND A CYCLOHEXANOL DERIVATIVE AS A SKIN REFRESHING AGENT

CROSS REFERENCE TO RELATED APPLICATIONS

This application is a National Phase filing under 35 U.S.C. § 371 of PCT/EP2015/079901 filed on Dec. 15, 2015; and this application claims priority to Application No. 1462421 filed in France on Dec. 15, 2014 under 35 U.S.C. § 119. The entire contents of each application are hereby incorporated by reference.

The present invention relates to the cosmetic use as a skin refreshing agent of the combination of at least one associative nonionic polyether polyurethane and at least one cyclohexanol derivative.

The present invention also relates to a cosmetic method for refreshing the skin, consisting in applying to the skin surface a composition comprising, in particular in a cosmetically acceptable medium:
 a) an aqueous phase; and
 b) at least one associative nonionic polyether polyurethane; and
 c) at least one cyclohexanol derivative.

The present invention also relates to a composition comprising, especially in a physiologically acceptable medium:
 a) at least one aqueous phase; and
 b) at least one associative nonionic polyether polyurethane; and
 c) at least one cyclohexanol derivative; and
 d) at least one antiperspirant active agent.

The present invention also relates to a method for the treatment of human perspiration, and optionally of body odors, which consists in applying to the surface of the skin a composition as described previously.

In the cosmetics field, it is well known to use for topical application antiperspirant products to treat perspiration and optionally body odor related to body perspiration. These products are generally available in the form of roll-ons, aerosols or sprays.

For consumers, it is interesting and pleasant to feel a refreshing effect when the product is applied. This fresh effect is generally produced by the presence of water and of a propellant gas in the antiperspirant product. However, the fresh effect felt after application disappears quickly.

A need remains to find an appropriate refreshing agent in particular for deodorant/antiperspirant products, whose effect can be long-lasting and reactivated during the day, particularly each time that the consumer sweats, without it being necessary to apply the product several times. This is even more useful during hot periods or in hot countries.

Among the refreshing agents commonly used in deodorant products, mention may be made of cyclohexanol derivatives and more particularly menthol. However, the effect obtained after application is fleeting and requires a repeated application to have a new freshness effect during the day.

The Applicant has discovered in a surprising manner that this goal could be met by using the combination of at least one associative nonionic polyether polyurethane and at least one cyclohexanol derivative. In fact, such a combination allows, in an unexpected manner, reactivation of the refreshment activity of the cyclohexanol in contact with water, moisture and particularly sweat and to be able to prolong the effect of freshness on the skin during the day if the consumer sweats without it being necessary to apply the product several times.

This discovery forms the basis of the present invention.

The present invention relates to the cosmetic use as a skin refreshing agent of the combination of at least one associative nonionic polyether polyurethane and at least one cyclohexanol derivative.

The present invention also relates to a cosmetic method for refreshing the skin, consisting in applying to the skin surface a composition comprising, in particular in a cosmetically acceptable medium:
 a) an aqueous phase; and
 b) at least one associative nonionic polyether polyurethane; and
 c) at least one cyclohexanol derivative.

The present invention also relates to a composition comprising, especially in a physiologically acceptable medium:
 a) at least one aqueous phase; and
 b) at least one associative nonionic polyether polyurethane; and
 c) at least one cyclohexanol derivative; and
 d) at least one antiperspirant active agent.

According to one particular form of the invention, the emulsion comprises a physiologically acceptable medium.

The term "refreshing active agent" is understood to mean any compound that can produce a feeling of freshness on the skin as soon as it is in contact with the skin by application by the topical route.

The refreshing agent(s) are present in concentrations ranging, for instance, from 0.1 to 1%, more preferentially from 0.1 to 0.5% by weight relative to the total weight of the formula.

For the purposes of the present invention, the term "physiologically acceptable medium" denotes a medium that is suitable for the topical administration of a composition, i.e. a medium which is odorless and has no unpleasant appearance, and which is perfectly compatible with the topical route of administration. Such a medium is considered to be "physiologically acceptable" in particular when it does not cause any tingling, tautness or redness unacceptable for the user.

The term "antiperspirant active agent" is intended to mean an active agent which, by itself, has the effect of reducing the flow of sweat, of reducing the sensation on the skin of moisture associated with human sweat and of masking human sweat.

The term "cyclohexanol derivative" is intended to mean any compound comprising in its structure the group having the structure

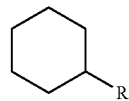

in which R denotes OH, a carboxylic, ester or carboxamide group;

R may form a dioxane or dioxolane ring connected to the cyclohexane ring in the following manner:

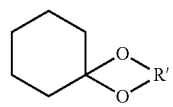

where R' represents a $C_2$-$C_6$ alkylene group having 1 to 3OH groups; where the cyclohexane ring can contain, as well as the R substituent on the other ring positions, other substituents such as linear or branched, saturated or unsaturated alkyl groups, linear or branched, saturated or unsaturated alkoxy groups.

The term "skin" is intended to mean the body, in particular armpits, face, feet and mucous membranes such as lips.

Associative Nonionic Polyether Polyurethane

In the sense of the present invention, "associative polymer" is understood to mean a hydrophilic polymer that in an aqueous medium can reversibly combine together or with other molecules. Their chemical structure more particularly comprises at least one hydrophilic region and at least one hydrophobic region.

The term "hydrophobic group" is intended to mean a radical or polymer comprising a saturated or unsaturated and linear or branched hydrocarbon-based chain. When the hydrophobic group denotes a hydrocarbon-based radical, it comprises at least 10 carbon atoms, preferably from 10 to 30 carbon atoms, in particular from 12 to 30 carbon atoms and more preferably from 18 to 30 carbon atoms. Preferentially, the hydrocarbon-based group is derived from a monofunctional compound.

By way of example, the hydrophobic group may be derived from a fatty alcohol, such as stearyl alcohol, dodecyl alcohol or decyl alcohol, or else from a polyalkylenated fatty alcohol, such as Steareth-100. It may also denote a hydrocarbon polymer, for instance polybutadiene.

The non-ionic polyether polyurethanes according to the invention generally comprise, in their chain, both hydrophilic blocks, usually of polyoxyethylene nature, and hydrophobic blocks that may be aliphatic sequences alone and/or cycloaliphatic and/or aromatic sequences.

Preferably, these polyether polyurethanes comprise at least two lipophilic hydrocarbon chains containing from 6 to 30 carbon atoms, separated by a hydrophilic block, the hydrocarbon chains possibly being pendant chains or chains at the end of the hydrophilic block. In particular, it is possible for one or more pendant chains to be provided. In addition, the polymer may comprise a hydrocarbon-based chain at one end or at both ends of a hydrophilic block.

The polyether polyurethanes may have multiple blocks, particularly in the form of triblocks. The hydrophobic blocks can be at each end of the chain (for example: triblock copolymer having a hydrophilic central block) or distributed both at the ends and in the chain (for example, multiblock copolymer). These same polymers can also be graft polymers or star polymers.

The nonionic polyether polyurethanes with fatty chains may be triblock copolymers whose hydrophilic block is a polyoxyethylenated chain including from 50 to 1000 oxyethylene groups.

The non-ionic polyether polyurethanes comprise a urethane linkage between the hydrophilic blocks, whence arises the name.

By extension, also included among the non-ionic polyether polyurethanes comprising a hydrophobic chain are those in which the hydrophilic blocks are linked to the hydrophobic blocks via other chemical bonds.

As examples of non-ionic polyether polyurethanes comprising a hydrophobic chain that may be used in the invention, it is also possible to use Rheolate 205® containing a urea functional group, sold by the company Rheox, or Rheolate® 208, 204 or 212, and also Acrysol RM 184®.

Mention may also be made of the product Elfacos T210® having a $C_{12}$-$C_{14}$ chain and the product Elfacos T212® having a $C_{18}$ alkyl chain from Akzo.

The product DW 1206B® from Rohm & Haas containing a $C_{20}$ alkyl chain and a urethane linkage, sold at a solids content of 20% in water, may also be used.

It is also possible to use the solutions or dispersions of these polymers, in particular in water or aqueous alcohol mediums. As examples of such polymers, mention may be made of Rhéolate® 255, Rhéolate® 278 and Rhéolate® 244 sold by Rheox. Use may also be made of the products DW 1206F and DW 1206J sold by the company Rohm & Haas.

The polyether polyurethanes that can be used according to the invention may also be chosen from those described in the article by G. Fonnum, J. Bakke and Fk. Hansen—Colloid Polym. Sci., 271, 380-389 (1993).

According to one particular form of the invention, a polyether polyurethane will be used that can be obtained by polycondensation of at least three compounds comprising (i) at least one polyethylene glycol comprising from 150 to 180 moles ethylene oxide, (ii) stearyl alcohol or decyl alcohol and (iii) at least one diisocyanate.

Such polyether polyurethanes are sold in particular by the company Rohm & Haas under the names Aculyn 46® and Aculyn 44®.

Aculyn 46® having the INCI name: PEG-150/Stearyl Alcohol/SMDI Copolymer is a polycondensate of polyethyleneglycol having 150 or 180 moles ethylene oxide, stearyl alcohol and methylene bis(4-cyclohexyl-isocyanate) (SMDI) at 15% by weight in a maltodextrin matrix (4%) and water (81%).

Aculyn 44® (PEG-150/Decyl Alcohol/SMDI Copolymer) is a polycondensate of polyethylene glycol comprising 150 or 180 mol of ethylene oxide, of decyl alcohol and of methylenebis(4-cyclohexyl isocyanate) (SMDI) at 35% by weight in a mixture of propylene glycol (39%) and water (26%).

According to one particularly preferred form of the invention, a polyether polyurethane will be used that can be obtained by polycondensation of at least three compounds comprising (i) at least one polyethylene glycol comprising from 150 to 180 moles of ethylene oxide, (ii) a polyoxyethylenated stearyl alcohol comprising 100 moles of ethylene oxide and (iii) a diisocyanate.

Such polyether polyurethanes are sold in particular by Elementis under the name SER-AD FX 1100®, Rheoluxe 811®, which is a polycondensat of polyethylene glycol having 136 mol of ethylene oxide, stearyl alcohol polyoxyethylenated with 100 mol of ethylene oxide and hexamethylene diisocyanate (HDI) having a weight-average molecular weight of 30,000 (INCI name: PEG-136/Steareth-1001/SMDI Copolymer).

The amount of the active substance in the compositions of the invention, the associative polyether polyurethane(s), may range for example from 0.01% to 3% by weight, preferably from 0.01% to 1.5% by weight relative to the total weight of the composition.

Cyclohexanol Derivatives

Among the cyclohexanol derivatives in accordance with the invention, mention may be made of in particular ketals having general formula (II) or (III)

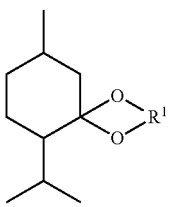

(II)

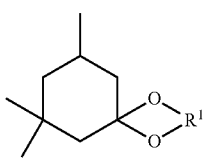

(III)

in which R¹ represents a $C_2$-$C_6$ 1,2-alkylene or 1,3-alkylene group having from 1 to 3 OH groups and forms with the two oxygen atoms a dioxane or dioxolane ring as described in U.S. Pat. No. 5,266,592. Among these compounds, mention may particularly be made of D,L-menthone 1,2-glycerol ketal having the structure:

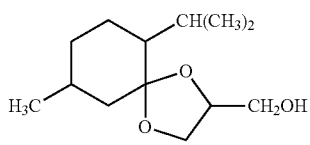

such as the product Frescolat MGA 600165® sold by the company Symrise.

Among the cyclohexanol derivatives in accordance with the invention, mention may be made of N-substituted p-menthane-3-carboxamides such as those described in U.S. Pat. No. 4,136,163 and having the following formula:

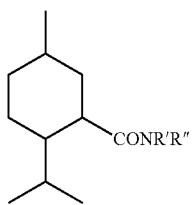

in which

R', taken individually, denotes a hydrogen or a hydrocarbon-based substituent containing up to 25 carbon atoms, R", taken individually, denotes a hydrogen or a hydrocarbon-based substituent containing up to 25 carbon atoms, with the proviso that when R' is hydrogen, R" can be an aryl substituent having up to 11 carbon atoms chosen from substituted phenyl, substituted or unsubstituted phenylalkyl, substituted or unsubstituted naphthyl, pyridyl;

R' and R" may also form, together with the nitrogen atom to which they are attached, a ring or heterocycle that can contain up to 25 carbon atoms such as piperidine, morpholine, etc.

As examples of R' and R" substituents, mention may be made of methyl, ethyl, propyl, isobutyl, n-decyl, cyclopropyl, cyclohexyl, cycloheptylm ethyl, 2-hydroxyethyl, 3-hydroxy-n-propyl, 6-hydroxy-n-hexyl, 2-am inoethyl, 2-acethoxyethyl, 2-ethylcarboxyethyl, 4-hydroxybut-2-ynyl, carboxym ethyl, etc. When R" is an aryl group, it may denote benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, etc.

Among these compounds, mention may particularly be made of

Methoxyphenyl menthane carboxamide having the structure

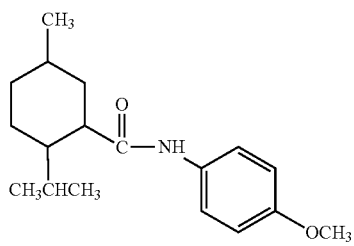

such as the product sold under the brand name Winsense WS-12® by the company Renessenz LLC;

Ethyl menthane carboxamide having the structure

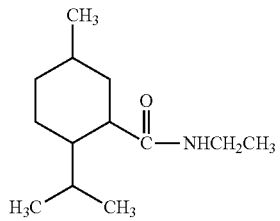

such as the product sold under the brand name OriStar WS3 (Orient Stars LLC) or Winsense WS-3 (Independent Chemical Corp).

Mention may also be made of 2-(2-alcoxy6&6methylethyl)-5-methylcyclohexanol compounds having the formula

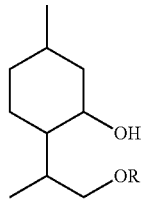

in which R denotes a linear or branched $C_1$-$C_5$ alkyl and its geometric isomers, particularly their (1R,2S,5R,8R) form.

Mention may also be made of cyclohexanol derivatives having the formula

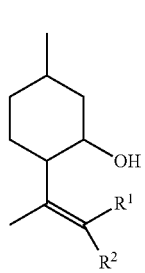

in which $R^1$ and $R^2$, independently of each other, denote a linear or branched $C_1$-$C_5$ alkyl substituent such as methyl, ethyl, n-propyl, isopropyl, n-butyl, isobutyl, tert-butyl, isopentyl, n-pentyl, sec-pentyl, tert-pentyl or neopentyl and more particularly methyl, ethyl, isopropyl, n-pentyl and even more preferentially methyl.

Mention may particularly be made of the compound 5-methyl-2-(1-methylvinyl)cyclohexan-1-ol such as those cited in U.S. Pat. No. 5,756,857 having the structure:

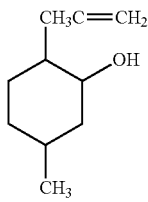

such as the product sold under the brand name Coolact PC® by the company Takasago International Corporation.

According to one particularly preferred embodiment, the cyclohexanol derivatives are chosen from those having the formula:

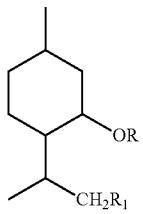

in which

R denotes a hydrogen atom; a linear or branched $C_1$-$C_5$ alkyl group, a linear or branched $C_1$-$C_5$ alkanediol group; a linear or branched $C_1$-$C_5$ carboxyhydroxyalkyl group.

$R_1$ denotes a hydrogen atom; a linear or branched $C_1$-$C_5$ alkyl group.

Among these compounds, mention may particularly be made of those for which $R_1$=H and R is hydrogen, propanediol, carboxyhydroxyethyl or carboxyhydroxypropyl and more particularly menthoxypropanediol ($R_1$=H and R=propanediol) having the structure:

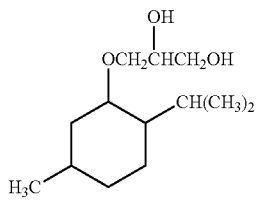

such as the product sold under the brand name TK 10® by the company Takasago International Corporation.

menthyl lactate ($R_1$=H and R=carboxyhydroxypropyl) having the structure

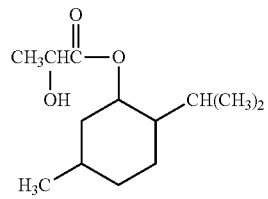

such as the product sold under the name Frescolat ML 620105® by the company Symrise;

menthol ($R_1$=R=H) or 5-methyl-2-(1-methylethyl)cyclohexanol or DL-menthol in synthetic form or of natural origin.

Menthol ($R_1$=R=H) also called 5-methyl-2-(1-methylethyl)cyclohexanol or DL-menthol or L-menthol will particularly be used, in isolated form in the form of mint extract and in particular in the form of essential oil; and mixtures thereof, and more particularly in isolated form.

Menthol can in particular be used in isolated form such as commercially available products sold under the names 620009 Menthol Laevo Pellets® by the company Symrise; AEC Menthol Crystals BP® and AEC Menthol Liquid Synthetic® by the company A & E Connock (Perfumery & Cosmetics) Ltd.); Custosense Menthol® by the company Custom Ingredients, Inc.; Jeen Menthol Crystal USP® by the company Jeen International Corporation; Menthol Crystals by the company Jan Dekker International; OriStar MC® by the company Orient Stars LLC; Unichem Ment® Universal Preserv-A-Chem, Inc.

Menthol according to the present invention may be used in the form of diverse varieties of mint extract such as *Mentha Aquatica, Mentha Arvensis, Mentha Canadensis, Mentha Pulegium, Mentha Rotundifolia, Mentha Spicata, Mentha Viridis*(Spearmint), *Mentha Piperita* (leaf, branches, stem, flower) such as extracts having the following INCI name:

*Mentha Aquatica* Extract,
*Mentha Aquatica* Flower/Leaf/Stem Extract,
*Mentha Aquatica* Flower/Leaf/Stem Water,
*Mentha Aquatica* Leaf Extract,
*Mentha Aquatica* Water,
*Mentha Arvensis* Branch/Leaf Extract,
*Mentha Arvensis* Extract,
*Mentha Arvensis* Flower/Leaf/Stem Extract,
*Mentha Arvensis* Flower/Leaf/Stem Water,
*Mentha Arvensis* Leaf Extract,
*Mentha Arvensis* Powder,
*Mentha Canadensis* Branch/Leaf Extract
*Mentha Pulegium* Extract
*Mentha Rotundifolia* Leaf Extract
*Mentha Spicata* Flower/Leaf/Stem Extract
*Mentha Spicata* Leaf Extract
*Mentha Suaveolens* Leaf Extract
*Mentha Viridis* (Spearmint) Extract
*Mentha Viridis* (Spearmint) Leaf
*Mentha Viridis* (Spearmint) Leaf Extract
*Mentha Viridis* (Spearmint) Leaf Juice
*Mentha Viridis* (Spearmint) Leaf Powder
*Mentha Viridis* (Spearmint) Leaf/Stem Water
Methoxyphenyl Menthane Carboxamide According to one particular form of the invention, the menthol as claimed in the present invention may also be used in the form of essential oil such as those having the following INCI name:

*Mentha Aquatica* Leaf Oil,
*Mentha Aquatica* Flower/Leaf/Stem Oil,
*Mentha Arvensis* Leaf Oil,
*Mentha Piperita* (Peppermint) Oil
*Mentha Pulegium* Oil
*Mentha Viridis* (Spearmint) Leaf Oil The amount of the cyclohexanol derivative will vary as a function of the type of delivery form and of the desired cosmetic or dermatological application.

The cyclohexanol derivative(s) in accordance with the invention are present in compositions, preferably, ranging from 0.1% to 1% by weight and preferentially from 0.1% to 0.5% by weight relative to the total weight of the formula.

Compositions

The present invention also relates to a cosmetic method for refreshing the skin, consisting in applying to the skin surface a composition comprising, in particular in a cosmetically acceptable medium:
  a) an aqueous phase; and
  b) at least one associative nonionic polyether polyurethane; and
  c) at least one cyclohexanol derivative.

The compositions may be presented in any aqueous delivery form intended to be applied to the skin for topical administration.

They can be presented in the form of ointments, creams, milks, pomades, impregnated pads, solutions, gels, sprays, lotions, or suspensions.

The cosmetic compositions may in particular be in the form of aqueous or aqueous alcohol solutions, dispersions of the solution type or dispersions of the lotion or serum type, emulsions of liquid or semi-liquid consistency of the milk type, obtained by dispersing a fatty phase in an aqueous phase (O/W), or vice versa (W/O), or suspensions or emulsions of soft, semi-solid or solid consistency of the cream type, or aqueous gels. They can be packaged in pressurized form such as aerosols in the presence of at least one propellant or sprays using a pump such as pump-action bottles.

These compositions are prepared according to the usual methods.

The compositions in accordance with the invention may in particular constitute creams for protecting, treating or caring for the face, for hands, for feet or for the body, body lotions for protection or care, after-sun lotions, lotions, gels or foams for skin care, anti-sun lotions, deodorant compositions containing a bactericidal agent, antiperspirant compositions, aftershave gels or lotions, or compositions against insect bites.

In a known manner, the cosmetic composition may also contain adjuvants that are common in the cosmetics field, such as hydrophilic or lipophilic gelling agents, hydrophilic or lipophilic active agents, preserving agents, antioxidants, solvents, fragrances, fillers, screening agents, bactericides and colorants. The amounts of these various adjuvants are those conventionally used in the field under consideration, for example from 0.01 to 20% of the total weight of the composition.

According to one particular form of the invention, the composition comprises, in particular in a physiologically acceptable medium
  a) at least one aqueous phase; and
  b) at least one associative nonionic polyether polyurethane; and
  c) at least one cyclohexanol derivative; and
  d) at least one antiperspirant active agent.

Antiperspirant Active Agents

Among the antiperspirant active agents, mention may be made of salts or complexes of aluminum and/or of zirconium, preferably chosen from aluminum halohydrates; aluminum zirconium halohydrates, complexes of zirconium hydroxychloride and of aluminum hydroxychloride with or without an amino acid, such as those described in U.S. Pat. No. 3,792,068.

Among the aluminum salts, mention may in particular be made of aluminum chlorohydrate in activated or unactivated form, aluminum chlorohydrex, the aluminum chlorohydrex-polyethylene glycol complex, the aluminum chlorohydrex-propylene glycol complex, aluminum dichlorohydrate, the aluminum dichlorohydrex-polyethylene glycol complex, the aluminum dichlorohydrex-propylene glycol complex, aluminum sesquichlorohydrate, the aluminum sesquichlorohydrex-polyethylene glycol complex, the aluminum sesquichlorohydrex-propylene glycol complex, aluminum sulfate buffered with sodium aluminum lactate.

Among the aluminum zirconium salts, mention may be made in particular of aluminum zirconium octachlorohydrate, aluminum zirconium pentachlorohydrate, aluminum zirconium tetrachlorohydrate and aluminum zirconium trichlorohydrate. The complexes of zirconium hydroxychloride and of aluminum hydroxychloride with an amino acid are generally known as ZAG (when the amino acid is glycine).

Among these products, mention may be made of the aluminum zirconium octachlorohydrex-glycine complexes, the aluminum zirconium pentachlorohydrex-glycine complexes, the aluminum zirconium tetrachlorohydrex-glycine complexes and the aluminum zirconium trichlorohydrex-glycine complexes.

Aluminum sesquichlorohydrate is in particular sold under the trade name Reach 301® by the company Summitreheis.

Among the aluminum and zirconium complexes, mention may be made of the complexes of zirconium hydroxychloride and of aluminum hydroxychloride with an amino acid such as glycine, having the INCI name: Aluminum Zirconium Tetrachlorohydrex Gly, for example the product sold under the name Reach AZP-908-SUF® by the company Summitreheis.

Use will more particularly be made of the aluminum chlorohydrate sold under the trade names Locron S FLA®, Locron P and Locron L.ZA by the company Clariant; under the trade names Microdry Aluminum Chlorohydrate®, Micro-Dry 323®, Chlorhydrol 50, Reach 103 and Reach 501 by the company Summitreheis; under the trade name Westchlor 200® by the company Westwood; under the trade name Aloxicoll PF 40® by the company Guilini Chemie; Cluron 50%® by the company Industria Quimica Del Centro; or Clorohidroxido Aluminio SO A 50%® by the company Finquimica.

As another active agent that can reduce the sensation of moisture on the skin related to human sweat, mention may be made of expanded perlite particles such as those obtained by the expansion process described in U.S. Pat. No. 5,002,698.

The perlites which can be used according to the invention are generally aluminosilicates of volcanic origin and have the composition:
  70.0-75.0% by weight of silica $SiO_2$
  12.0-15.0% by weight of aluminum oxide $Al_2O_3$
  3.0-5.0% of sodium oxide $Na_2O$
  3.0-5.0% of potassium oxide $K_2O$
  0.5-2% of iron oxide $Fe_2O_3$
  0.2-0.7% of magnesium oxide $MgO$ 0.5-1.5% of calcium oxide CaO 0.05-0.15% of titanium oxide $TiO_2$ Preferably, the perlite particles used will be ground; in this case, they are known as Expanded Milled Perlite (EMP). They preferably have a particle size defined by a median diameter D50 ranging from 0.5 to 50 µm and preferably from 0.5 to 40 µm.

Preferably, the perlite particles used have an untamped apparent density at 25° C. ranging from 10 to 400 kg/m$^3$ (standard DIN 53468) and preferably from 10 to 300 kg/m$^3$.

Preferably, the expanded perlite particles according to the invention have a water absorption capacity, measured at the wet point, ranging from 200% to 1500% and preferably from 250% to 800%.

The wet point corresponds to the amount of water which has to be added to 1 g of particle in order to obtain a homogeneous paste. This method derives directly from the oil uptake method applied to solvents. The measurements are taken in the same manner by means of the wet point and the flow point, which have, respectively, the following definitions:

wet point: mass expressed in grams per 100 g of product corresponding to the production of a homogeneous paste during the addition of a solvent to a powder;

flow point: mass expressed in grams per 100 g of product above which the amount of solvent is greater than the capacity of the powder to retain it. This is reflected by the production of a more or less homogeneous mixture which flows over the glass plate.

The wet point and the flow point are measured according to the following protocol: Protocol for measuring the water absorption 1) Equipment Used Glass plate (25×25 mm)

Spatula (wooden shaft and metal part, 15×2.7 mm)

Silk-bristled brush

Balance

2) Procedure

The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) with the spatula.

The weight of solvent needed to obtain the wet point is noted. Further solvent is added and the weight which makes it possible to reach the flow point is noted. The average of three tests will be determined.

The expanded perlite particles sold under the trade names Optimat 1430 OR or Optimat 2550 by the company World Minerals will be used in particular.

Mention may also be made of talcs or magnesium silicates such as that sold under the name Luzenac 15 M00® by the company Luzenac.

Among the antiperspirant active agents, use will more particularly be made of aluminum chlorohydrate, aluminum sesquichlorohydrate, perlite, and mixtures thereof.

The antiperspirant active agents may be present in the composition according to the invention in a proportion of from 0.001% to 40% by weight relative to the total weight of the composition, and preferably in a proportion of from 0.1% to 25% by weight.

According to one particular form of the invention, the compositions comprise at least one additional deodorant active agent.

Deodorant Active Agents

The term "antiperspirant active agent" is intended to mean any aluminum salt or complex which, by itself alone, has the effect of reducing the flow of sweat, of reducing the sensation on the skin of moisture associated with human sweat and of masking human sweat.

The deodorant active agents may be bacteriostatic agents or bactericides that act on underarm odor micro-organisms, such as 2,4,4'-trichloro-2'-hydroxydiphenyl ether (®Triclosan), 2,4-dichloro-2'-hydroxydiphenyl ether, 3',4',5'-trichlorosalicylanilide, 1-(3',4'-dichlorophenyl)-3-(4'-chlorophenyl)urea (®Triclocarban) or 3,7,11-trimethyldodeca-2,5,10-trienol (®Farnesol); quaternary ammonium salts such as cetyltrimethylammonium salts, cetylpyridinium salts, DPTA (1,3-diaminopropanetetraacetic acid), 1,2-decanediol (SymClariol from the company Symrise); glycerol derivatives, for instance caprylic/capric glycerides (Capmul MCM® from Abitec), glyceryl caprylate or caprate (Dermosoft GMCY® and Dermosoft GMC®, respectively from Straetmans), polyglyceryl-2 caprate (Dermosoft DGMC® from Straetmans), and biguanide derivatives, for instance polyhexamethylene biguanide salts; chlorhexidine and salts thereof; 4-phenyl-4,4-dimethyl-2-butanol (Symdeo MPP® from Symrise); zinc salts such as zinc salicylate, zinc gluconate, zinc pidolate, zinc sulfate, zinc chloride, zinc lactate or zinc phenolsulfonate; salicylic acid and derivatives thereof such as 5-n-octanoylsalicylic acid.

C) Odor Absorbers

The deodorant active agents may be odor absorbers such as zinc ricinoleates or sodium bicarbonate; metallic or silver or silver-free zeolites, or cyclodextrins and derivatives thereof. They may also be chelating agents such as Dissolvine GL-47-S® from Akzo Nobel, EDTA and DPTA. They may also be a polyol such as glycerol or 1,3-propanediol (Zemea Propanediol sold by Dupont Tate and Lyle Bioproducts).

d) Enzymatic Inhibitors

The deodorant active agents may also be enzyme inhibitors such as triethyl citrate; or alum.

In the event of incompatibility and/or to stabilize them, for example, some of the active agents mentioned above may be incorporated into spherules, especially ionic or nonionic vesicles and/or nanoparticles (nanocapsules and/or nanospheres).

The deodorant active agents may be present in the composition according to the invention in a proportion of from 0.001% to 40% by weight relative to the total weight of the composition, and preferably in a proportion of from 0.1% to 25% by weight.

Delivery Forms

The antiperspirant compositions in accordance with the present invention may in particular be packaged in pressurized form in an aerosol device or in a pump-action bottle; packaged in a device equipped with a perforated wall, in particular a grating; packaged in a device equipped with a ball applicator ("roll-on"); packaged in the form of wands (sticks). In this regard, they contain the ingredients generally used in products of this type, which are well known to those skilled in the art.

According to another particular form of the invention, the compositions according to the invention may be solid, in particular in wand or stick form.

The term "solid composition" is intended to mean that the measurement of the maximum force measured by texturometry during the penetration of a probe into the sample of formulation must be at least equal to 0.25 newtons, in particular at least equal to 0.30 newtons and especially at least equal to 0.35 newtons, assessed under precise measurement conditions as follows.

The formulations are poured hot into jars 4 cm in diameter and 3 cm deep. Cooling is performed at ambient temperature. The hardness of the formulations produced is measured after an interval of 24 hours. The jars containing the samples are characterized by texturometry using a texture analyzer such as the machine sold by the company Rheo TA-XT2, according to the following protocol: a stainless-steel ball probe 5 mm in diameter is brought into contact with the sample at a speed of 1 mm/s. The measurement system detects the interface with the sample, with a detection threshold equal to 0.005 newtons. The probe sinks 0.3 mm into the sample, at a rate of 0.1 mm/s. The measuring machine records the change in force measured in compression over time, during the penetration phase. The hardness of the sample corresponds to the average of the maximum force values detected during penetration, over at least three measurements.

Aqueous Phase

The compositions according to the invention intended for cosmetic use may comprise at least one aqueous phase. They are in particular formulated as aqueous lotions or as water-in-oil or oil-in-water emulsions or as multiple emulsions (oil-in-water-in-oil or water-in-oil-in-water triple emulsions (such emulsions are known and described, for example, by C. Fox in "Cosmetics and Toiletries"—November 1986—Vol. 101—pages 101-112)).

The aqueous phase of a composition according to the invention comprises water and optionally a water-soluble solvent.

The water can in particular be a floral water, a mineral water and/or a source water such as Eau de Vichy, Eau de Lucas or Eau de la Roche Posay.

In the present invention, the term "water-soluble solvent" denotes a compound that is liquid at ambient temperature and water-miscible (miscibility with water of greater than 50% by weight at 25° C. and atmospheric pressure).

The water-soluble or water-miscible solvents comprise short-chain, for example $C_1$-$C_4$, monoalcohols, such as ethanol or isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. Use will more particularly be made of propylene glycol and glycerol, and propane-1, 3-diol.

The composition according to the invention preferably has a pH ranging from 3 to 9, according to the support chosen.

Emulsifiers

Oil-in-water Emulsifiers

Mention may be made, as emulsifiers which can be used in the oil-in-water emulsions or oil-in-water-in-oil triple emulsions, for example, of non-ionic emulsifiers, such as oxyalkylenated (more particularly polyoxyethylenated) esters of fatty acids and of glycerol; oxyalkylenated esters of fatty acids and of sorbitan; oxyalkylenated (oxyethylenated and/or oxypropylenated) esters of fatty acids; oxyalkylenated (oxyethylenated and/or oxypropylenated) ethers of fatty alcohols; sugar esters, such as sucrose stearate; and mixtures thereof, such as the mixture of glyceryl stearate and PEG-40 stearate.

Mention may also be made of fatty alcohol/alkylpolyglycoside emulsifying mixtures, such as are described in applications WO92/06778, WO95/13863 and WO98/47610, for instance the commercial products sold by the company SEPPIC under the name Montanov®.

Water-in-oil Emulsifiers

Among the emulsifiers which can be used in the water-in-oil emulsions, mention may be made, by way of example, of alkyl dimethicone copolyols, for instance Cetyl PEG/PPG-10/1 Dimethicone and more particularly the mixture Cetyl PEG/PPG-10/1 Dimethicone and Dimethicone (INCI name), such as the product sold under the trade name Abil EM90 by the company Goldschmidt, or alternatively the mixture (Polyglyceryl-4 stearate and Cetyl PEG/PPG-10 (and) Dimethicone (and) Hexyl Laurate), such as the product sold under the trade name Abil WE09 by the company Goldschmidt. Mention may also be made of Lauryl PEG-9 polydimethylsiloxyethyl dimethicone, such as the commercial product KF-6038® from Shin-Etsu.

Among the water-in-oil emulsifiers, mention may also be made of dimethicone copolyols, for instance PEG-18/PPG-18 Dimethicone and more particularly the mixture Cyclopentasiloxane (and) PEG-18/PPG-18 Dimethicone (INCI name), such as the product sold by the company Dow Corning under the trade name Silicone DC 5225 C or KF-6040 from Shin-Etsu.

Among the water-in-oil emulsifiers, mention may also be made of nonionic emulsifiers derived from fatty acids and polyols, alkyl polyglycosides (APGs), sugar esters and mixtures thereof.

As nonionic emulsifiers derived from fatty acids and polyols, use may be made especially of fatty acid esters of polyols, the fatty acid especially containing a $C_8$-$C_{24}$ alkyl chain, and the polyols being, for example, glycerol and sorbitan.

Fatty acid esters of polyols that may especially be mentioned include isostearic acid esters of polyols, stearic acid esters of polyols, and mixtures thereof, in particular isostearic acid esters of glycerol and/or sorbitan.

Stearic acid esters of polyols that may in particular be mentioned include the polyethylene glycol esters, for instance PEG-30 Dipolyhydroxystearate, such as the product sold under the name Arlacel P135 by the company ICI.

Glycerol and/or sorbitan esters that may be mentioned, for example, include polyglyceryl isostearate, such as the product sold under the name Isolan GI 34 by the company Goldschmidt; sorbitan isostearate, such as the product sold under the name Arlacel 987 by the company ICI; sorbitan glyceryl isostearate, such as the product sold under the name Arlacel 986 by the company ICI, the mixture of sorbitan isostearate and polyglyceryl isostearate (3 mol) sold under the name Arlacel 1690 by the company Uniqema, and mixtures thereof.

The emulsifier can also be chosen from alkylpolyglycosides having an HLB of less than 7, for example those represented by the following general formula (1):

$$R-O-(G)_x \qquad (1)$$

in which R represents a branched and/or unsaturated alkyl radical comprising from 14 to 24 carbon atoms, G represents a reduced sugar comprising 5 or 6 carbon atoms, and x is a value ranging from 1 to 10 and preferably from 1 to 4, and G especially denotes glucose, fructose or galactose.

The unsaturated alkyl radical may comprise one or more ethylenic unsaturations, and in particular one or two ethylenic unsaturations.

As alkyl polyglycosides of this type, mention may be made of the alkyl polyglucosides (G=glucose in formula (I)), and in particular the compounds of formula (I) in which R more particularly represents an oleyl radical (unsaturated C18 radical) or isostearyl radical (saturated C18 radical), G denotes glucose, x is a value ranging from 1 to 2, in particular isostearyl glucoside or oleyl glucoside, and mixtures thereof. This alkyl polyglucoside may be used as a mixture with a coemulsifier, more especially with a fatty alcohol and especially a fatty alcohol containing the same fatty chain as that of the alkyl polyglucoside, i.e. comprising from 14 to 24 carbon atoms and containing a branched and/or unsaturated chain, for example isostearyl alcohol when the alkyl polyglucoside is isostearyl glucoside, and oleyl alcohol when the alkyl polyglucoside is oleyl glucoside, optionally in the form of a self-emulsifying composition, as described, for example, in document WO-A-92/06778. Use may be made, for example, of the mixture of isostearyl glucoside and isostearyl alcohol, sold under the name Montanov WO 18 by the company SEPPIC.

Mention may also be made of succinic-terminated polyolefins, for instance esterified succinic-terminated polyisobutylenes and salts thereof, especially the diethanolamine salts, such as the commercial products sold under the names Lubrizol 2724, Lubrizol 2722 and Lubrizol 5603 by the company Lubrizol or the commercial product Chemcinnate 2000.

The total amount of emulsifiers in the composition will preferably be, in the composition according to the invention, at active material contents ranging from 1% to 8% by weight and more particularly from 2% to 6% by weight, relative to the total weight of the composition.

Oil Phase

The compositions according to the invention may contain at least one water-immiscible organic liquid phase, known as a fatty phase. This phase generally comprises one or more hydrophobic compounds that make said phase water-immiscible. Said phase is liquid (in the absence of structuring agent) at room temperature (20-25° C.). Preferentially, the water-immiscible organic liquid phase in accordance with the invention generally comprises at least one volatile oil and/or one non-volatile oil and optionally at least one structuring agent.

The term "oil" is intended to mean a fatty substance that is liquid at ambient temperature (25° C.) and atmospheric pressure (760 mmHg, i.e. 105 Pa). The oil may be volatile or non-volatile.

For the purposes of the invention, the term "volatile oil" is intended to mean an oil that is capable of evaporating on contact with the skin or the keratin fiber in less than one hour, at ambient temperature and atmospheric pressure. The volatile oils of the invention are volatile cosmetic oils that are liquid at ambient temperature, with a non-zero vapor pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" is intended to mean an oil that remains on the skin or the keratin fibre at ambient temperature and atmospheric pressure for at least several hours, and that in particular has a vapor pressure of less than $10^{-3}$ mmHg (0.13 Pa).

The oil may be chosen from any oil, preferably physiologically acceptable oils and in particular cosmetically acceptable oils, especially mineral, animal, plant or synthetic oils; in particular volatile or non-volatile hydrocarbon-based oils and/or silicone oils and/or fluorinated oils, and mixtures thereof.

More precisely, the term "hydrocarbon-based oil" means an oil mainly comprising carbon and hydrogen atoms and optionally one or more functions chosen from hydroxyl, ester, ether and carboxylic functions. Generally, the oil has a viscosity of from 0.5 to 100 000 mPa·s, preferably from 50 to 50 000 mPa·s and more preferably from 100 to 300 000 mPa·s.

As examples of volatile oils that may be used in the invention, mention may be made of:

volatile hydrocarbon-based oils chosen from hydrocarbon-based oils containing from 8 to 16 carbon atoms, and especially $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Use may also be made of other volatile hydrocarbon-based oils, such as petroleum distillates, in particular those sold under the name Shell Solt by the company Shell; and volatile linear alkanes, such as those described in Patent Application DE10 2008 012 457 by the company Cognis.

volatile silicones, for instance linear or cyclic volatile silicone oils, in particular those with a viscosity of ≤8 centistokes ($8\times10^{-6}$ m$^2$/s), and containing in particular from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane;

and mixtures thereof.

As examples of non-volatile oils that may be used in the invention, mention may be made of:

hydrocarbon-based oils of animal origin, such as perhydrosqualene;

hydrocarbon-based oils of plant origin, such as liquid triglycerides of fatty acids containing from 4 to 24 carbon atoms, for instance caprylic/capric acid triglycerides such as those sold by the company Stéarinerie Dubois or those sold under the names Miglyol 810, 812 and 818 by the company Dynamit Nobel;

linear or branched hydrocarbons of mineral or synthetic origin, such as liquid paraffins and derivatives thereof, petroleum jelly, polydecenes, polybutenes, hydrogenated polyisobutene, such as Parleam, or squalane;

synthetic ethers containing from 10 to 40 carbon atoms, synthetic esters, especially of fatty acids, isononyl isononanoate, isopropyl myristate, isopropyl palmitate, $C_{12}$-$C_{15}$ alcohol benzoates, hexyl laurate, diisopropyl adipate, 2-ethylhexyl palmitate, 2-octyldodecyl stearate, 2-octyldodecyl erucate, isostearyl isostearate;

fatty alcohols that are liquid at ambient temperature, containing a branched and/or unsaturated carbon-based chain containing from 12 to 26 carbon atoms, for instance octyldodecanol, isostearyl alcohol, 2-butyloctanol, 2-hexyldecanol, 2-undecylpentadecanol or oleyl alcohol;

higher fatty acids such as oleic acid, linoleic acid or linolenic acid;

carbonates;

acetates;

citrates;

fluorinated oils that are optionally partially hydrocarbon-based and/or silicone-based, for instance fluorosilicone oils, fluoropolyethers and fluorosilicones as described in the document EP-A-847 752;

silicone oils, for instance non-volatile polydimethylsiloxanes (PDMSs); phenyl silicones, for instance phenyl trimethicones, phenyl dimethicones, phenyltrimethylsiloxydiphenylsiloxanes, diphenyl dimethicones, diphenylmethyldiphenyltrisiloxanes, 2-phenylethyl trimethylsiloxysilicates, and mixtures thereof.

According to one particularly preferred form of the invention, the composition is in the form of an oil-in-water emulsion comprising:

a) a continuous aqueous phase, and b) an oil phase dispersed in the aqueous phase, and b) at least one associative nonionic polyether polyurethane as defined previously, and d) at least one cyclohexanol derivative as defined previously, and e) at least one mixture comprising at least one alkylpolyglycoside whose alkyl chain is linear or branched and comprises from 12 to 22 carbon atoms and at least one linear or branched fatty alcohol, having from 12 to 22 carbon atoms;

f) at least one antiperspirant active agent as defined previously.

The composition may be presented in the form of a cream, distributed in a tube or a grating; and more particularly in the form of a roll-on.

Alkylpolyglucoside/Fatty Alcohol Mixture

These compositions in accordance with the invention comprise at least one mixture of:

a) at least one alkylpolyglycoside whose alkyl chain is linear or branched and comprises from 12 to 22 carbon atoms and b) at least one linear or branched fatty alcohol having from 12 to 22 carbon atoms.

In the composition, this mixture behaves as an emulsifying agent.

For the purposes of the present invention, the term "alkylpolyglycoside" means an alkylmonosaccharide (degree of polymerization 1) or an alkylpolyglycoside (degree of polymerization greater than 1).

Preferentially the emulsifying fatty alcohol/alkylpolyglycoside mixture contains:

(a) from 5% to 60% by weight of alkylpolyglycoside(s);

(b) from 95% to 40% by weight of fatty alcohol(s) relative to the total weight of said emulsifying mixture.

The alkylpolyglycosides may be used alone or in the form of mixtures of several alkylpolyglycosides. They generally correspond to the following structure:

R(O)(G)$_x$ in which the R substituent is a linear or branched $C_{12}$-$C_{22}$ alkyl substituent, G is a saccharide residue and x ranges from 1 to 5, preferably from 1.05 to 2.5 and more preferentially from 1.1 to 2.

The saccharide residue may be chosen from glucose, dextrose, saccharose, fructose, galactose, maltose, maltotriose, lactose, cellobiose, mannose, ribose, dextran, talose, allose, xylose, levoglucan, cellulose and starch. More preferentially, the saccharide residue denotes glucose.

It should also be noted that each unit of the polysaccharide part of the alkylpolyglycoside may be in α or β isomer form, in L or D form, and the configuration of the saccharide residue may be of furanoside or pyranoside type.

It is, of course, possible to use mixtures of alkylpolysaccharides, which may differ from each other in the nature of the borne alkyl unit and/or the nature of the bearing polysaccharide chain.

Concerning the fatty alcohols that must be used, alone or in mixtures, in combination with alkylpolysaccharides in the emulsifying mixtures in accordance with the invention, these can be linear or branched fatty alcohols of synthetic or alternatively of natural origin, for example alcohols derived from plant material (coconut, palm kernel, palm, etc.) or animal material (tallow, etc.). Needless to say, other long-chain alcohols may also be used, for instance ether alcohols or Guerbet alcohols. Finally, use may also be made of certain fractions of alcohols of varying length of natural origin, for instance coconut ($C_{12}$ to $C_{16}$) or tallow ($C_{16}$ to $C_{18}$) or compounds such as diols or cholesterol.

According to a preferred embodiment of the present invention, the fatty alcohol(s) used are chosen from those containing from 12 to 22 carbon atoms and even more preferentially from 12 to 18 carbon atoms.

As particular examples of fatty alcohols that may be used in the context of the present invention, mention may be made especially of lauryl alcohol, cetyl alcohol, myristyl alcohol, stearyl alcohol, isostearyl alcohol, palmityl alcohol, oleyl alcohol, behenyl alcohol and arachidyl alcohol, which may thus be taken alone or as mixtures.

In addition, it is particularly advantageous, according to the present invention, to use together a fatty alcohol and an alkylpolysaccharide whose alkyl part is identical to that of the selected fatty alcohol.

The fatty alcohol/alkylpolyglycoside emulsifying mixtures as defined above are known as such. They are described in applications WO92/06778, WO95/13863 and WO98/47610 and prepared according to the preparation processes indicated in these documents.

Among the particularly preferred fatty alcohols/alkylpolyglycoside mixtures, mention may be made of the products sold by the company SEPPIC under the name Montanov®, such as the following mixtures:

Cetylstearyl alcohol/cocoyl glucoside—Montanov 82®

Arachidyl alcohol and behenyl alcohol/arachidyl glucoside—Montanov 802®

Myristyl alcohol/myristyl glucoside—Montanov 14®

Cetylstearyl alcohol/cetylstearyl glucoside—Montanov 68®

$C_{14}$-$C_{22}$ alcohols/$C_{12}$-$C_{20}$ alkyl glucoside—Montanov L®

Cocoyl alcohol/cocoyl glucoside—Montanov S®

Isostearyl alcohol/isostearyl glucoside—Montanov WO 18®

Fatty alcohol/alkylpolyglycoside mixtures chosen from the following will be preferred:

Cetylstearyl alcohol/cetylstearyl glucoside;

$C_{14}$-$C_{22}$ alcohols/$C_{12}$-$C_{20}$ alkyl glucoside and even more particularly the $C_{14}$-$C_{22}$ alcohols/$C_{12}$-$C_{20}$ alkyl glucoside mixture such as the commercial product $C_{14}$-$C_{22}$ alcohol/$C_{12}$-$C_{20}$ alkyl glucoside—Montanov L®.

The fatty alcohol/alkylpolyglycoside mixture is preferably present in emulsions in accordance with the invention in concentrations ranging from 0.5% to 15% by weight and more preferentially from 1% to 10% by weight relative to the total weight of the composition.

According to one particular form of the invention, the emulsion comprises:

a) at least one continuous aqueous phase; and b) at least one oil phase dispersed in said aqueous phase; and c) at least one $C_{14}$-$C_{22}$ alcohol/$C_{12}$-$C_{20}$ alkyl glucoside mixture; and d) at least one polycondensate of polyethylene glycol containing 136 mol of ethylene oxide, stearyl alcohol polyoxyethylenated with 100 mol of ethylene oxide and hexamethylene diisocyanate (HDI) with a weight-average molecular weight (Mw) of 30,000 (INCI name: PEG-136/Steareth-100I/SMDI Copolymer) and e) menthol, and f) at least one aluminum and/or zirconium salt or complex, particularly aluminum chlorhydrate.

According to another particularly preferred form of the invention, the composition is in the form of a water-in-oil emulsion packaged in an aerosol, comprising:

a) a continuous oil phase, and b) an aqueous phase dispersed in the oil phase, and c) at least one associative nonionic polyether polyurethane as defined previously, and d) at least one refreshing agent chosen from cyclohexanol derivatives as defined previously and, f) at least one antiperspirant active agent as defined previously, and g) at least one propellant.

According to one particular form of the invention, the composition comprises at least one water-in-oil emulsifier chosen from alkyl dimethicone copolyols such as Cetyl PEG/PPG-10/1 Dimethicone and more particularly the Cetyl PEG/PPG-10/1 Dimethicone and Dimethicone mixture (INCI name), such as the product sold under the trade name Abil EM90 by the company Goldschmidt, or alternatively the mixture (Polyglyceryl-4 stearate and Cetyl PEG/PPG-10 (and) Dimethicone (and) Hexyl Laurate), such as the product sold under the trade name Abil WE09 by the company Goldschmidt. Mention may also be made of Lauryl PEG-9 polydimethylsiloxyethyl dimethicone, such as the commercial product KF-6038 from Shin-Etsu.

According to one particular form of the invention, the oil phase preferably comprises at least one non-volatile silicone oil and more preferably a non-volatile polydimethylsiloxane (PDMS) (INCI name: Dimethicone).

In this case, the non-volatile silicone oils are preferably present in contents ranging from 5 to 30% by total weight and more preferentially from 10 to 25% by weight relative to the total weight of the oil phase.

According to one particular form of the invention, the composition comprises:

a) a continuous oil phase comprising at least one involatile silicone oil and more preferentially an involatile polydimethylsiloxane (PDMS); and b) an aqueous phase dispersed in the oil phase, and c) at least one polycondensate of polyethylene glycol containing 136 mol of ethylene oxide, stearyl alcohol polyoxyethylenated with 100 mol of ethylene oxide and hexamethylene diisocyanate (HDI) with a weight-average molecular weight (Mw) of 30,000 (INCI name: PEG-136/Steareth-100I/SMDI Copolymer) and e) menthol, and f) at least one aluminum and/or zirconium salt or complex, particularly aluminum chlorhydrate.

g) at least one propellant.

Propellant

The propellants are advantageously chosen from dimethyl ether (DME), volatile hydrocarbons such as n-butane, propane, isobutane, and mixtures thereof, optionally with at least one chlorinated and/or fluorinated hydrocarbon. Among the latter, mention may be made of the compounds sold by the company DuPont de Nemours under the names Freon® and Dymel®, and in particular monofluorotrichloromethane, difluorodichloromethane, tetrafluorodichloroethane and 1,1-difluoroethane, sold in particular under the trade name Dymel 152 A by the company DuPont. Carbon dioxide, nitrous oxide, nitrogen or compressed air may also be used as propellant.

The composition containing the deodorant active agent(s) and the propellant(s) may be in the same compartment or in different compartments in the container.

According to the invention, the concentration of propellant preferably ranges between 55% and 95% by weight relative to the total weight of the pressurized composition. More preferably, the concentration of propellant ranges from 70% to 85% by weight relative to the total weight of the pressurized composition.

The term "pressurized composition" is understood to mean the total fluid+gas composition contained in the container.

The invention also relates to a cosmetic process for treating human perspiration, and optionally the body odors associated with human perspiration, which consists in applying to the surface of the skin an effective amount of the cosmetic composition as described previously.

The application time of the cosmetic composition on the surface of the skin may range from 0.5 to 10 seconds and preferably from 1 to 5 seconds.

The cosmetic composition in accordance with the invention may be applied several times to the surface of the skin.

In particular, the cosmetic treatment process according to the invention consists in applying to the surface of the armpits an effective amount of the cosmetic composition as described above.

The invention also relates to the use of said composition for the cosmetic treatment of human perspiration.

Another subject of the present invention is an aerosol device consisting of a container comprising an aerosol composition as defined previously and of a means for dispensing said composition.

The dispensing means, which forms a part of the aerosol device, generally consists of a dispensing valve controlled by a dispensing head, which itself comprises a nozzle via which the aerosol composition is vaporized. The container containing the pressurized composition may be opaque or transparent. It may be made of glass, of polymer or of metal, optionally coated with a protective varnish coat.

The examples which follow illustrate the present invention without limiting the scope thereof. The amounts are expressed as weight percentages relative to the total weight of the composition.

EXAMPLE 1

Roll-on (W/O Emulsion)

| Ingredients (INCI name) | Example 1 (invention) | Example 2 (outside the invention) |
|---|---|---|
| STEARETH-100/PEG-136/HDI COPOLYMER (RHEOLUXE 811) | 1.0 | — |
| C14-22 ALCOHOLS (and) C12-20 ALKYL GLUCOSIDE (MONTANOV L) | 3.0 | 3.0 |
| ALUMINUM CHLORHYDRATE in aqueous solution at 50% by weight (CLURON 50% ®) | 30 | 30 |
| PERLITE (OPTIMAT 1430 OR ®) | 1.0 | 1.0 |
| PHENOXYETHANOL | 0.7 | 0.7 |

-continued

| Ingredients (INCI name) | Example 1 (invention) | Example 2 (outside the invention) |
|---|---|---|
| FRAGRANCE | 1.0 | 1.0 |
| MENTHOL-L (620009 MENTHOL LAEVO PELLETS ®) | 0.2 | 0.2 |
| WATER | qs 100 | qs 100 |

Procedure:

In the main tank, at 80° C. with turbomixer stirring, water and the associative polyurethane polyether Steareth-100/PEG-136/HDI Copolymer were added, the phase composed of (C14-C22 Alcohols (and) C12-C20 Alkyl glucoside, Dimethicone, Menthol) was added, stirred with turbine for 20 minutes. The mixture was cooled to 45° C. The aluminum chlorhydrate, perlite and fragrance were added and the mixture was stirred with blades then cooled to 25° C.

EXAMPLE 2

Aerosol Formula (Water-in-silicone Emulsion)

| Ingredients (INCI name) | Fluid Example 3 (invention) | Fluid Example 4 (outside the invention) |
|---|---|---|
| DIMETHICONE (BELSIL DM 10 ®) 10 cst | 20.0 | 20.0 |
| ALUMINUM CHLOROHYDRATE in aqueous solution at 50% by weight (CLURON 50% ®) | 30.0 | 30.0 |
| LAURYL PEG-9 POLYDIMETHYLSILOXYETHYL DIMETHICONE (KF-6038 ®) | 1.0 | 1.0 |
| PERLITE (OPTIMAT 1430 OR ®) | 0.25 | 0.25 |
| FRAGRANCE | 5.0 | 5.0 |
| Phenoxyethanol | 0.7 | 0.7 |
| STEARETH-100/PEG-136/HDI COPOLYMER (RHEOLUXE 811 ®) | 0.5 | — |
| DIMETHICONE (and) DIMETHICONOL (XIAMETER PMX-1503 FLUID ®) | 2.0 | 2.0 |
| MENTHOL-L (620009 MENTHOL LAEVO PELLETS ®) | 1.0 | 1.0 |
| WATER | qs 100 | qs 100 |

Procedure

At ambient temperature (20-25° C.), the Dimethicone (and) Dimethiconol, Phenoxyethanol, Dimethicone, Steareth-100/PEG-136/HDI Copolymer were added to the manufacturing tank, with turbomixer stirring. Once the mixture was homogeneous, with turbomixer stirring and at ambient temperature, the aqueous phase (water+aluminum chlorhydrate) was added at a temperature of 40° C., with continued stirring for 10 minutes, and then the mixture was cooled to 25° C. The perlite, fragrance and menthol were added with stirring, then the mixture was homogenized for 5 minutes.

The fluid was incorporated into a classic aerosol device such as an aerosol device from Précision APSL® with direct output, diameter 0.41 mm.

| Ingredients (INCI name) | Aerosol Example 3 (invention) | Aerosol Example 4 (invention) |
|---|---|---|
| Fluid | 20.0 | 20.0 |
| Isobutane | 30.0 | 30.0 |

Demonstration of the Effect of Progressive Menthol Release: Analysis According to the Head Space Technique 1) Qualitative Analytical Method (Present or Not) for Menthol Released by Adding Water After Application to Skin and Drying:

Qualitative analyses were run on each of the compositions from examples 1 to 4, after application on the forearm.

Preparing the Sample and Sampling:

About 150 mg of each formula was deposited on the skin in a thin layer then left to dry for 1 h in air.

The sample from the head space (volatile portion) is taken from a developed device composed of a collection tube made of Tenax TA®, connected to a glass bell used to confine the sample and from the other to a pump.

The analysis was run by thermodesorption from the Tenax TA® tube then gas chromatography coupled with a mass spectrometer.

2) Analytical Method for Residual Menthol in the Formula After Application onto an Inert Substrate and Drying:

Qualitative analyses were run on each of the compositions from examples 1 to 4, after application on an inert substrate.

Sample Preparation:

A thin layer of 150 mg of formula was applied to an FHLP-type filter (diameter 47 mm). These deposits were left at ambient temperature (20-25° C.) for 1 hour of drying in air. Each filter+formula pair was extracted with 2 mL of ethanol. The solution obtained containing menthol was analyzed.

The analyses were run using gas chromatography coupled with a mass spectrometer.

Results

| Presence of menthol in the head space | Roll-on Example 1 (invention) | Roll-on Example 2 (outside the invention) | Aerosol Example 3 (invention) | Aerosol Example 4 (outside the invention) |
|---|---|---|---|---|
| T = 1 hour after drying | +++ | + | +++ | + |
| 1st spray with water T = 1.5 hour | +++ | + | +++ | + |
| 2nd spray with water T = 2 hours | +++ | − | +++ | − |
| 3rd spray with water T = 2.5 hours | ++ | − | ++ | − |
| 4th spray with water T = 3 hours | ++ | − | ++ | − |

+++ high presence of menthol
++ moderate presence of menthol
+ low presence of menthol
− menthol absent The qualitative analyses on the film remaining on the substrate show that after one hour of drying, the film formed by the formulas 1 and 3 of the invention containing menthol, combined with the associative polyether polyurethane, present high menthol content whereas formulas 2 and 4 that do not contain the associative polyether polyurethane present low menthol content;

that after spraying with water at T=1.5 h and T=2 hours, the film formed by formulas 1 and 3 of the invention containing menthol, combined with the associative polyether polyurethane, still presents a high menthol content, by contrast with formulas 2 and 4 that do not contain polyether polyurethane;

that after spraying with water at T=2.5 h and T=3 hours, the film formed by formulas 1 and 3 of the invention containing menthol, combined with the associative polyether polyurethane, presents a moderate menthol content, by contrast with formulas 2 and 4 that do not contain polyether polyurethane.

The invention claimed is:

1. A cosmetic method for refreshing the skin, which comprises applying to the skin surface a composition comprising as a skin refreshing agent a combination of at least one associative nonionic polyether polyurethane and at least one cyclohexanol derivative represented by the following formulae:

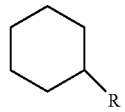

in which R denotes OH, a carboxylic group, ester group or carboxamide group; or

R forms a dioxane or dioxolane ring connected to the cyclohexane ring as follows:

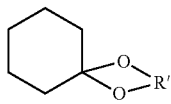

where R' represents a $C_2$-$C_6$ alkylene group having 1 to 3 OH groups; and wherein the cyclohexane ring is optionally substituted with at least one member selected from the group consisting of a linear or branched, saturated or unsaturated alkyl group, linear or branched, and saturated or unsaturated alkoxy group;

wherein the amount of the at least one associative nonionic polyether polyurethane is 0.01 to 3% by weight based upon the weight of the composition and the amount of the at least one cyclohexanol derivative is 0.1 to 1% by weight based upon the weight of the composition.

2. The cosmetic method as claimed in claim 1, where the associative nonionic polyether polyurethane includes in its chain both hydrophilic and hydrophobic blocks selected from the group consisting of aliphatic sequences, cycloaliphatic sequences and aromatic sequences and mixtures thereof.

3. The cosmetic method as claimed in claim 2, where the associative nonionic polyether polyurethane includes at least two lipophilic hydrocarbon-based chains containing from 6 to 30 carbon atoms, separated by a hydrophilic block, where the hydrocarbon-based chains may be pendant chains or chains at the end of a hydrophilic block.

4. The cosmetic method as claimed in claim 3, where the associative nonionic polyether polyurethane is in the form of a triblock whose hydrophilic block is a polyoxyethylenated chain including 50 to 1000 oxyethylenated groups.

5. The cosmetic method as claimed in claim 2, where the associative nonionic polyether polyurethane is obtained by polycondensation of at least three compounds comprising (i) at least one polyethylene glycol comprising from 150 to 180 mol of ethylene oxide, (ii) a polyoxyethylenated stearyl alcohol comprising 100 mol of ethylene oxide, and (iii) a diisocyanate.

6. The cosmetic method as claimed in claim 5, where the associative nonionic polyether polyurethane is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight (Mw) of 30,000 (INCI name: PEG-136/Steareth-1001/SMDI Copolymer).

7. The cosmetic method as claimed in claim 1, where the cyclohexanol derivative is chosen from those having the formula:

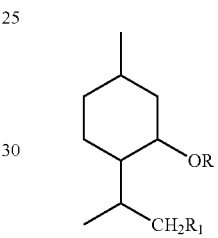

in which

R denotes a hydrogen atom; a linear or branched $C_1$-$C_5$ alkyl group, a linear or branched $C_1$-$C_5$ alkanediol group; a linear or branched $C_1$-$C_5$ carboxyhydroxyalkyl group, $R_1$ denotes a hydrogen atom; a linear or branched $C_1$-$C_5$ alkyl group.

8. The cosmetic method as claimed in claim 7, where the cyclohexanol derivative is selected from the group of menthol in the isolated form, menthol in the form of mint extract and mixtures thereof.

9. A cosmetic method for refreshing the skin, which comprises applying to the skin surface a composition comprising:

a) at least one aqueous phase, b) and at least one refreshing agent which comprises a combination of b') at least one associative nonionic polyether polyurethane and b") at least one cyclohexanol derivative represented by the following formulae:

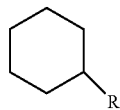

in which R denotes OH, a carboxylic group, ester group or carboxamide group; or

R forms a dioxane or dioxolane ring connected to the cyclohexane ring as follows:

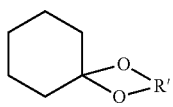

where R' represents a $C_2$-$C_6$ alkylene group having 1 to 3 OH groups; and wherein the cyclohexane ring is optionally substituted with at least one member selected from the group consisting of a linear or branched, saturated or unsaturated alkyl group, linear or branched, and saturated or unsaturated alkoxy group;

wherein the amount of the at least one associative nonionic polyether polyurethane is 0.01 to 3% by weight based upon the weight of the composition and the amount of the at least one cyclohexanol derivative is 0.1 to 1% by weight based upon the weight of the composition.

10. The method as claimed in claim 9, where the amount of the at least one substance associative nonionic polyether polyurethane ranges from 0.01 to 3% by weight relative to the total weight of the composition.

11. The method as claimed in claim 9, where the at least one refreshing agent is present in concentrations ranging from 0.1 to 1%, relative to the total weight of the composition.

12. A composition comprising:
a) at least one aqueous phase;
b) and at least one refreshing agent which comprises a combination of
b') at least one associative nonionic polyether polyurethane and
b") at least one cyclohexanol derivative represented by the following formulae:

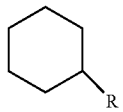

in which R denotes OH, a carboxylic group, ester group or carboxamide group; or

R forms a dioxane or dioxolane ring connected to the cyclohexane ring as follows:

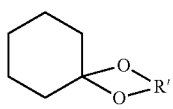

where R' represents a $C_2$-$C_6$ alkylene group having 1 to 3 OH groups; and wherein the cyclohexane ring is optionally substituted with at least one member selected from the group consisting of a linear or branched, saturated or unsaturated alkyl group, linear or branched, and saturated or unsaturated alkoxy group and c) at least one antiperspirant active agent;

wherein the amount of the at least one associative nonionic polyether polyurethane is 0.01 to 3% by weight based upon the weight of the composition and the amount of the at least one cyclohexanol derivative is 0.1 to 1% by weight based upon the weight of the composition.

13. The composition as claimed in claim 12, where the antiperspirant agent is chosen from aluminum and/or zirconium salts or complexes, perlite, talcs and mixtures thereof.

14. The composition as claimed in claim 12, which is in the form of an oil-in-water emulsion comprising,
a) a continuous aqueous phase; and
b) an oil phase dispersed in the aqueous phase, and
c) said at least one associative nonionic polyether polyurethane; and
d) said at least one cyclohexanol derivative, and
e) at least one mixture comprising at least one alkylpolyglycoside whose alkyl chain is linear or branched and comprises from 12 to 22 carbon atoms and at least one linear or branched fatty alcohol, having from 12 to 22 carbon atoms; and
f) said at least one antiperspirant active agent.

15. The composition as claimed in claim 14, comprising
a) at least one continuous aqueous phase; and
b) at least one oil phase dispersed in said aqueous phase; and
c) at least one $C_{14}$-$C_{22}$ alcohols/$C_{12}$-$C_{20}$ alkyl glucoside mixture; and
d) at least one polycondensate of polyethylene glycol containing 136 mol of ethylene oxide, stearyl alcohol polyoxyethylenated with 100 mol of ethylene oxide and hexamethylene diisocyanate (HDI) with a weight-average molecular weight (Mw) of 30,000 (INCI name: PEG-136/Steareth-100/SMDI Copolymer); and
e) menthol, and
f) at least one aluminum and/or zirconium salt or complex.

16. The composition as claimed in claim 12, which is an oil-in-water emulsion packaged in an aerosol, comprising:
a) said continuous oil phase, and
b) said aqueous phase dispersed in the oil phase, and
c) said at least one associative nonionic polyether polyurethane and
d) said at least one cyclohexanol derivative and
f) said at least one antiperspirant active agent and
g) at least one propellant.

17. The composition as claimed in claim 16, comprising:
a) wherein said continuous oil phase comprises at least one involatile silicone oil; and
b) said aqueous phase dispersed in the oil phase, and
c) at least one polycondensate of polyethylene glycol containing 136 mol of ethylene oxide, stearyl alcohol polyoxyethylenated with 100 mol of ethylene oxide and hexamethylene diisocyanate (HDI) with a weight-average molecular weight (Mw) of 30,000 (INGI name: PEG-136/Steareth-100/SMDI Copolymer) and
e) menthol, and
f) at least one aluminum and/or zirconium salt or complex and
g) said at least one propellant.

18. A method for the treatment of body odors and optionally of human perspiration, which comprises applying to the surface of a keratin material an emulsion as defined in claim 12.

19. The cosmetic method as claimed in claim 2, where the cyclohexanol derivative is chosen from those having the formula:

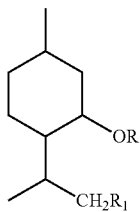

in which
R denotes a hydrogen atom; a linear or branched $C_1$-$C_5$ alkyl group, a linear or branched $C_1C_5$ alkanediol group; a linear or branched $C_i$-$0_5$ carboxyhydroxyalkyl group,
$R_1$ denotes a hydrogen atom; a linear or branched $C_1$-$C_5$ alkyl group.

20. The cosmetic method as claimed in claim 3, where the cyclohexanol derivative is chosen from those having the formula:

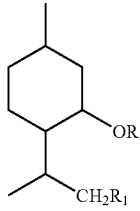

in which
R denotes a hydrogen atom; a. linear or branched $C_1$-$C_5$ alkyl group, a linear or branched $C_1$-$C_5$ alkanediol group; a linear or branched $C_1$-$C_5$ carboxyhydroxyalkyl group,
$R_1$ denotes a hydrogen atom; a linear or branched $C_1$-$C_5$ alkyl group.

21. The cosmetic method as claimed in claim 1, wherein the amount of the at least one associative nonionic polyether polyurethane is 0.01 to 1.5% by weight based upon the weight of the composition and the amount of the at least one cyclohexanol derivative is 0.1 to 0.5% by weight based upon the weight of the composition.

22. The cosmetic method as claimed in claim 9, wherein the amount of the at least one associative nonionic polyether polyurethane is 0.01 to 1.5% by weight based upon the weight of the composition and the amount of the at least one cyclohexanol derivative is 0.1 to 0.5% by weight based upon the weight of the composition.

23. The composition as claimed in claim 12, wherein the amount of the at least one associative nonionic polyether polyurethane is 0.01 to 1.5% by weight based upon the weight of the composition and the amount of the at least one cyclohexanol derivative is 0.1 to 0.5% by weight based upon the weight of the composition.

24. The cosmetic method as claimed in claim 1, wherein the skin surface is at least one of armpits, face, feet and lips.

25. The cosmetic method as claimed in claim 9, wherein the skin surface is at least one of armpits, face, feet and lips.

* * * * *